United States Patent [19]

Yukawa et al.

[11] 4,271,267

[45] Jun. 2, 1981

[54] PREPARATION OF L-TRYTOPHAN BY FERMENTATION

[75] Inventors: Hideaki Yukawa; Kazuoki Osumi; Terukatsu Nara; Yoshihiro Takayama, all of Ami, Japan

[73] Assignee: Mitsubishi Petrochemical Co., Ltd., Tokyo, Japan

[21] Appl. No.: 101,041

[22] Filed: Dec. 6, 1979

[30] Foreign Application Priority Data

Dec. 11, 1978 [JP] Japan ................. 53-152052

[51] Int. Cl.$^3$ ............................... C12P 13/22
[52] U.S. Cl. ..................... 435/108; 435/881; 435/247
[58] Field of Search ................. 435/108, 881

[56] References Cited

U.S. PATENT DOCUMENTS 3,036,958  5/1962  Asai et al. ............... 435/108

OTHER PUBLICATIONS

Derwent Abstract 04937 of Japan (Unexamined application), 135284/75; 10/27/75.

*Primary Examiner*—Lionel M. Shapiro
*Attorney, Agent, or Firm*—Sughrue, Rothwell, Mion, Zinn and Macpeak

[57] ABSTRACT

A process for preparing L-tryptophan by fermentation which comprises cultivating on a medium containing ethanol as the main carbon source a microorganism of the genus Serratia that utilizes ethanol and has the ability to produce L-tryptophan, and recovering the accumulated L-tryptophan from the culture.

1 Claim, No Drawings

PREPARATION OF L-TRYTOPHAN BY FERMENTATION

BACKGROUND OF THE INVENTION

1. Field of the Invention

This invention relates to the preparation of L-tryptophan by fermentation.

2. Description of the Prior Art

L-Tryptophan is useful as an essential amino acid, and an economical process for producing it on an industrial scale is in demand. Conventionally, L-tryptophan has been prepared by fermentation on a medium containing a precursor (e.g., indole, anthranilic acid or serine) (described in, for example, Japanese Patent Publication No. 27353/71) or by the "direct fermentation method" which does not use such precursor (described in, for example, Japanese Patent Publication No. 38795/76). The direct fermentation method that does not require a precious precursor is considered advantageous for production of the tryptophan on an industrial scale.

SUMMARY OF THE INVENTION

As a result of various studies on an advantageous process for producing L-tryptophan by the direct fermentation method, it has been found that a significant amount of L-tryptophan is produced when a microorganism of the genus Serratia that utilizes ethanol and has the ability to produce L-tryptophan is cultivated on a medium containing ethanol as the main carbon source. Tryptophan has been recovered and purified. The conventional processes for producing an amino acid by fermentation with ethanol used as the main carbon source include the production of L-glutamic acid (Japanese Patent Publication Nos. 15746/72 and 675/72), the production of amino acids such as proline, alanine, glycine, valine, leucine, isoleucine, aspartic acid, lysine, cerin, threonine, homocerin, phenylalanine, o-ethylhomocerin, etc. (Japanese Patent Publication No. 29/72), the production of L-isoleucine (Japanese Patent Application (OPI) Nos. 130592/76 and 75386/78 (The term "OPI" as used herein refers to a "published unexamined Japanese patent application")) and the production of serine (Japanese Patent Application (OPI) Nos. 130985/77 and 87083/73). However, the only process ever known for producing L-tryptophan by fermentation with ethanol used as the main carbon source is that of using Brevibacterium, Corynebacterium, Arthrobacter, Microbacterium or Bacillus (Japanese Patent Application (OPI) No. 135284/75), and no process is known that uses an ethanol-utilizing microorganism of the genus Serratia.

DETAILED DESCRIPTION OF THE INVENTION

The microorganisms that can be used in the process of this invention include all microorganisms that belong to the genus Serratia and have the ability to produce and accumulate L-tryptophan utilizing ethanol whether they are wild strains isolated from the natural habitat or artificially mutated varieties. An illustrative example of such microorganism is *Serratia marcescens* MT-5 which was derived by induction from *Serratia marcescens* variety MAY-110 (FERM-P No. 3521) as a strain resistant to 5-methyl-DL-tryptophan. The MT-5 strain has been deposited with the Fermentation Research Institute, Agency of Industrial Science and Technology, Japan, and accepted under FERM-P No. 4735.

The mutated strains resistant to 5-methyl-DL-tryptophan, particularly *S. marcescens* MT-5, are obtained in the following manners.

Microorganisms, particularly the MAY-110 strain, are subjected to an ultraviolet ray irradiation treatment or treated with chemicals (such as N-methyl-N'-nitro-N-nitrosoguanidine) to cause variation. For example, the MAY-110 strain is chemically treated using N-methyl-N'-nitro-N-nitrosoguanidine. The concentration of N-methyl-N'-nitro-N-nitrosoguanidine is 100 μg/ml (tris-maleate buffer solution of pH 7.0 is used), and the treatment time is 15 minutes at 30° C.

The strain suspension solution is coated on a flat plate culture (0.2% carbon, 0.7% ammonium sulfate, 0.05% $KH_2PO_4$, 0.05% $K_2HPO_4$, 0.05% $MgSO_4.7H_2O$, 2 mg/l NaCl, 2 mg/l $CaCl_2.2H_2O$, 2 mg/l $FeSO_4.7H_2O$, 2 mg/l $ZnSO_4.7H_2O$, 2 mg/l $MnSO_4.4$-$6H_2O$, 200 μg/l biotin, 100 μg/l thiamine hydrochloride, 800 mg/l 5-methyl-DL-tryptophan, 2.0% agaragar, 2 V/V% ethanol (added after sterilization)) and inoculated at 30° C. for several days. Large colonies formed are separated again planted on the above-mentioned flat plate culture containing 5-methyl-DL-tryptophan, the strains which are again grown are examined visually and separated to obtain the desired mutated strain.

*Serratia marcescens* variety MAY-110 is already disclosed in Japanese Patent Application (OPI) No. 130985/77 and its microbiological properties are as follows:

I. Morphological properties

Short rods (0.8-1.2×1.0-2.0μ). With peritrichous flagella and is motile. No spores present. Gram-negative. Not acid-fast.

II. State of growth

1. Broth agar culture medium

The colony conical, pink in color, and has wavy periphery.

2. Broth agar streak culture medium

Filiform or slightly echinate.

3. Broth medium

Membrane formed. Turbidity in the liquid.

4. Broth agar stab culture medium

Grows well on the surface. Internal growth filiform.

III. Growth conditions

1. Growth temperature: suitable range 27°-35° C., growth range 12°-38° C.
2. Growth pH: optimum range pH 6-8, growth range pH 5-10
3. Behavior toward oxygen: aerobic
4. Utilization of ammonium salt: yes
5. Utilization of urea: no
6. Utilization of nitrate: no
7. Halotolerance: grows well in broth medium containing 3% NaCl IV Physiological properties and others 1. Does not liquefy gelatin.
2. Causes no change in litmus milk.
3. Reduction of nitrate: weak
4. Formation of indole: no
5. Formation of hydrogen sulfide: no
6. Hydrolysis of starch: no
7. Voges-Proskauer reaction: negative
8. Methyl red reaction: negative
9. Formation of catalase: positive
10. Formation of urease: negative
11. Fermentation of carbohydrates Neither acid nor gas was formed from the following carbohydrates: arabinose, xylose, glucose, mannose, galactose, fructose, maltose, saccharose, lactose, milibiose, cellobiose, trehalose, raffinose, starch, inositol, mannitol, sorbitol, glycerin, aesculin and salicin 12. Vitamin requirement: no
13. Utilization of citric acid: no
14. Denitrification reaction: positive The above microorganism is a Gram-negative bacillus which does not form any spore and has peritrichous flagella which give it motility. It is characterized by the formation of a pink colony. Therefore, the microorganism obviously belongs to the genus Serratia as judged by Bergy's Manual, but in view of the absence of the formation of acid from various glycides, it is considered a variety of *Serratia marcescens* and designated *Serratia marcescens* variety MAY-110.

The specific embodiment of the process of this invention is now described. Ethanol is used as the carbon source of the medium, and its initial concentration is properly selected from the range of about 1 to 5% V/V depending on the strain used. Any loss in ethanol due to digestion is to be compensated with care taken so that its concentration is not detrimental to the growth of the culture or the formation of L-tryptophan. Ammonium sulfate, ammonium nitrate, ammonium chloride, ammonium phosphate, urea or other suitable substances are used as a nitrogen source depending on the strain's ability to utilize nitrogen in an amount of about 0.5 to 5% W/V. The medium may contain required amounts (about 0.01 to 5% W/V) of other organic nutrients such as amino acids, corn steep liquor, seasoned liquid and yeast extract, inorganic salts, and vitamins. The cultivating temperature ranges from 20° to 37° C., preferably from 25° to 35° C., and the pH from 4 to 10, preferably from 6 to 8, with optimum conditions being selected depending upon the strain used. The incubation generally requires 2 to 7 days. After incubation, the resulting L-tryptophan is recovered from the fermentation liquor using an ion exchange resin, activated charcoal, concentration and precipitation, or any other conventional method.

The process of this invention is hereunder described in greater detail by reference to the following example. Determination of the product L-tryptophan was made by a bioassay using *Leuconostoc mesenteroides* (American Type Culture Commission, Rockville, Maryland, ATCC No. 8042. See *JIKKEN NOGEI KAGAKU* (*Experimental Agricultural Chemistry*), the first volume, pages 284–285, Tokyo University, Faculty of Agriculture, Department of Agricultural Chemistry, published by Asakura Shobo (1960). Before incubation, the amount of L-tryptophan contained in the medium was determined by the bioassay, and the result was subtracted from the determination of the resulting L-tryptophan to obtain the true yield of the product.

EXAMPLE

A preculture medium was prepared that consisted of 2.0 g urea, 7.0 g ammonium sulfate, 0.5 g $KH_2PO_4$, 0.5 g $K_2HPO_4$, 0.5 g $MgSO_4.7H_2O$, 0.5 g yeast extract, 0.5 g Casamino acid, 2 mg $FeSO_4.7H_2O$, 2 mg $MnSO_4.4H_2O$, 200 μg biotin, 100 μg thiamine hydrochloride and 1 liter of tap water. Aliquots of 10 ml each of the medium were proportioned in a plurality of test tubes 24 mm in diameter, sterilized at 120° C. for 10 minutes, 0.2 ml of ethanol added under aseptic conditions, inoculated with *Serratia marcescens* MT-5, and subjected to shake culture at 30° C. for 2 days. Aliquots of 10 ml each of a medium having the same composition as the preculture medium were proportioned in another set of test tubes 24 mm in diameter, sterilized at 120° C. for 10 minutes, 0.2 g of dry sterilized calcium carbonated added, 0.2 ml of ethanol added, inoculated with 0.2 ml of the preculture solution, and subjected to shake culture at 30° C. for 7 days. Any loss in the ethanol due to digestion was compensated by additional ethanol, with care taken so that the ethanol concentration would not exceed 3% V/V. After the 7-day incubation, 12 mg/l of L-tryptophan was accumulated, which was recovered by the conventional method.

While the invention has been described in detail and with reference to specific embodiments thereof, it will be apparent to one skilled in the art that various changes and modifications can be made therein without departing from the spirit and scope thereof.

What is claimed is:

1. A process for preparing L-tryptophan by fermenation which comprises
    cultivating on a medium containing ethanol as the main carbon source a microorganism of the strain *Serratia marcescens* MT-5 that utilizes ethanol and has the ability to produce L-tryptophan, and
    recovering the accumulated L-tryptophan from the culture.

* * * * *